United States Patent [19]
Kaneyasu et al.

[11] Patent Number: 5,124,021
[45] Date of Patent: Jun. 23, 1992

[54] SOLID ELECTROLYTE GAS SENSOR AND METHOD OF MEASURING CONCENTRATION OF GAS TO BE DETECTED IN GAS MIXTURE

[75] Inventors: Kazunari Kaneyasu; Takeshi Nakahara, both of Fujisawa, Japan

[73] Assignee: Tokuyama Soda Kabushiki Kaisha, Tokuyama, Japan

[21] Appl. No.: 634,738

[22] Filed: Dec. 27, 1990

[51] Int. Cl.⁵ .............................. G01N 27/26
[52] U.S. Cl. ......................... 204/425; 204/426
[58] Field of Search .......................... 204/425, 426

[56] References Cited

U.S. PATENT DOCUMENTS

| | | | |
|---|---|---|---|
| 4,502,939 | 3/1985 | Holfelder et al. | 204/426 |
| 4,938,861 | 7/1990 | Kurosawa et al. | 204/425 |
| 4,950,380 | 8/1990 | Kurosawa et al. | 204/425 |

Primary Examiner—John Niebling
Assistant Examiner—Bruce F. Bell
Attorney, Agent, or Firm—Sherman and Shalloway

[57] ABSTRACT

A solid electrolyte gas sensor and a method for the measurement of a concentration of a gas to be detected in a gas mixture. The sensor has (A) a screen for controlling a permeation rate of the gas, which comprises (a1) a first solid electrolytic membrane selectively permeable to ions derived from a specific gas, and (a2) a plurality of first porous conductors being present on both front and reverse surfaces of the first solid electrolytic membrane and electrically connected with each other so as to give a potential required for oxidation and reduction of the gas, and (B) a detection portion for detecting a permeation amount of ions derived from the gas, which comprises (b1) a second solid electrolytic membrane, (b2) a plurality of second porous conductors, and (b3) means of electrically measuring an amount of ions derived from the gas which permeates the second solid electrolytic membrane. The amount of ions which permeate the first solid electrolytic membrane of the above screen (A) per unit time is smaller than an amount of ions which permeate the second solid electrolytic membrane of the above detection portion (B) per unit time under conditions that the sensor is in operation; and all of ions which permeate the second solid electrolytic membrane of the above detection portion (B) are those which have permeated the first solid electrolytic membrane of the above screen (A).

11 Claims, 6 Drawing Sheets

SOLID ELECTROLYTE GAS SENSOR AND METHOD OF MEASURING CONCENTRATION OF GAS TO BE DETECTED IN GAS MIXTURE

DETAILED DESCRIPTION OF THE INVENTION

This invention relates to a solid electrolyte gas sensor and a method of measuring a concentration of a gas in a gas mixture. More specifically, it relates to a solid electrolyte gas sensor having such a structure that an electrode reaction rate of a gas to be detected (hereinafter sometimes referred to as a gas G) in a detection portion of the solid electrolyte gas sensor and a rate of discharging a generated molecular gas from said detection portion are greater than a rate of feeding the gas to said detection portion, and a method of measuring a concentration of a gas G in a gas mixture on the basis of the principle of said solid electrolyte gas sensor.

A solid electrolyte gas sensor of a limiting current type is conventionally known. It is known that the advantages of the solid electrolyte gas sensor of a limiting current type are that it can measure oxygen gas in a wider concentration range than an oxygen gas sensor of a concentration cell type, that it can be decreased in size, and that it requires no reference gas.

In a report entitled "High-Temperature Oxygen Sensors Based on Electrochemical Pumping" at pages 136 to 154 of Fundamentals and Applications of Chemical Sensors published by American Chemical Society in 1986, the principle and basic structure of the solid electrolyte gas sensor of a limiting current type are discussed by reference to an oxygen gas sensor. That is, the solid electrolyte gas sensor of a limiting current type has a basic structure in which an electrode of the detection portion thereof is covered with a cap having a capillary or a porous ceramic such that an electrode reaction rate of a gas G in the detection portion and a discharge rate of a generated molecular gas from said detection portion are controlled to be greater than a rate of feeding the gas G to said detection portion. A mixture gas which contains the gas to be detected reaches an electrode of the detection portion through the capillary or pores of the porous ceramic in the above structure. It is therefore made possible to control the rate of feeding the mixture gas to be measured and, consequently, the gas G to the detection portion by suitably changing the size of the capillary or the diameter of the pores.

The detection portion generally has a structure in which there are disposed an ionically conductive solid electrolyte and two electrodes sandwiching said electrolyte. The gas G reaches one electrode (with which to generate ions derived from the gas G) of the above two to form ions under an electrode reaction. The ions formed reach the other electrode through the ionically conductive solid electrolyte. The ions are converted to a molecular gas under an electrode reaction which proceeds on the "other" electrode reversely to the above ionization reaction, and discharged from this electrode to a space surrounding this electrode. Therefore, when the rate of feeding the gas which is to reach the electrode with which to generate ions derived from the gas G is controlled to be smaller than the rate of the electrode reaction for the generation of ions on said electrode and the rate of forming a molecular gas from said ions under the reverse electrode reaction and discharging it, a current measured in the detection portion always shows a constant limiting current value. As a result, it is made possible to find a concentration of the gas G in the mixture gas on the basis of the above limiting current value.

However, the solid electrolyte gas sensor of a limiting current type uses the above structure, in which the electrode of the detection portion is covered with a cap having a capillary or a porous ceramic, in order to control the rate of feeding a gas to the detection portion and, consequently, control a diffusion rate. Therefore, when the gas mixture containing a gas G, which passes through the capillary or the pores of the porous ceramic, contains contaminants, e.g. suspended solids or mist, such suspended solids and the like gradually adhere to the interior of the capillary or the pores and prevent the gas G from reaching the detection portion by diffusion. When a diffusion resistance to the gas G is increased to obtain a clear limiting current value, it is desirable to lengthen a gas diffusion path within the capillary or the pores. In such a case in particular, the above suspended solids or mist contained in the gas mixture have a greater influence, and as a result, it is eventually impossible to obtain an exact concentration of the gas G as a measurement value.

It is an object of this invention to provide a novel solid electrolyte gas sensor.

It is another object of this invention to provide a solid electrolyte gas sensor of a limiting current type, which is capable of accurately measuring a concentration (or partial pressure) of a gas G for a long period of time even if a gas mixture containing said gas G contains solid or viscous suspended matter.

It is further another object of this invention to provide a solid electrolyte gas sensor of a limiting current type, which permits the feeding of a gas G without using a gas diffusion resistance within pores as a rate controlling step.

It is yet another object of this invention to provide a solid electrolyte gas sensor of limiting current type, which has a structure in which ions formed by an electrode reaction of a gas G contained in a gas mixture to be measured are allowed to migrate to an opposite side through a solid electrolytic membrane, gasified by an electrode reaction reverse to the above electrode reaction, and fed to a detection portion of the sensor.

Further, it is another object of this invention to provide a solid electrolyte gas sensor of a limiting current type, which has a structure in which a gas G contained in a mixture gas to be measured is fed to a detection portion of the sensor through a gas control screen structured such that a solid electrolytic membrane is sandwiched with two porous conductors.

It is still further another object of this invention to provide a method of measuring a gas concentration by measuring a current limiting value by means of a solid electrolyte gas sensor having such a constitution that a gas G is fed to a detection portion of the sensor through a gas control screen having a structure in which a solid electrolytic membrane selectively permeable to ions formed by an electrode reaction of the gas G contained in a mixture gas to be measured is placed between two porous conductors and these two conductors are electrically connected with each other so as to give, therebetween, a potential equivalent to or higher than an oxidation or reduction potential of the gas G, and that the gas G is discharged at a greater discharge rate than a rate of feeding the gas G in the detection portion.

Other objects and advantages of this invention will be apparent from the following description.

The above objects and advantages of this invention are firstly achieved by a solid electrolyte gas sensor for the measurement of a concentration of a gas to be detected in a gas mixture, which has:

(a) a screen for controlling a permeation rate of the gas G, which comprises:
 (a1) a first solid electrolytic membrane selectively permeable to ions derived from a specific gas to be detected, and
 (a2) a plurality of first porous conductors being present on both front and reverse surfaces of said first solid electrolytic membrane and electrically connected with each other so as to give a potential required for oxidation and reduction of said gas G, and
(B) a detection portion for detecting a permeation amount of ions derived from the gas to be detected, which comprises;
 (b1) a second solid electrolytic membrane selectively permeable to ions derived from a specific gas to be detected,
 (b2) a plurality of second porous conductors being present on both front and reverse surfaces of said second solid electrolytic membrane and electrically connected with each other so as to give a potential required for oxidation and reduction of said gas G, and
 (b3) means of electrically measuring an amount of ions derived from the gas G which permeates the second solid electrolytic membrane; wherein:
(C) an amount of ions which permeate the first solid electrolytic membrane of the above screen (A) per unit time is smaller than an amount of ions which permeate the second solid electrolytic membrane of the above detection portion (B) per unit time under conditions that the sensor is in operation: and
(D) all of ions which permeate the second solid electrolytic membrane of the above detection portion (B) are those which have permeated the first solid electrolytic membrane of the above screen (A).

In the present specification, the term "ions derived from the gas G" means the following two types of ions: ions formed by ionization of a gas itself to be detected such as oxygen ion ($O^{2-}$) when the gas to be detected is an oxygen gas, and ions formed by an electrode reaction of a gas to be detected on the porous conductor such as hydrogen ion when the gas to be detected is carbon monoxide.

As described above, the solid electrolyte gas sensor of this invention basically has (A) a screen with which to control a permeation rate of a gas G, and (B) a detection portion in which to detect an amount of the gas G which has permeated.

The major characteristic structural feature of the solid electrolyte gas sensor of this invention is the above screen (A). Since the solid electrolyte gas sensor of this invention is provided with the screen (A), (C) the amount of ions which permeate the first solid electrolytic membrane of the above screen (A) per unit time is made smaller than the amount of ions which permeate the second solid electrolytic membrane of the above detection portion (B) per unit time under conditions that the sensor is in operation. In other words, the amount of ions derived from the gas G, which reach the detection portion (B), is controlled due to the presence of the screen (A). In the gas sensor of this invention, it is naturally required, as described above, that (D) all of ions which permeate the second solid electrolytic membrane of the above detection portion (B) should be those which have permeated the first solid electrolytic membrane of the above screen (A) so that the amount of ions to be detected in the detection portion (B) is controlled by means of the screen (A).

The structure of the gas sensor of this invention will be detailed hereinafter. In this connection, a conventional gas sensor, particularly a solid electrolyte gas sensor of a limiting current type, will be explained first by reference to FIGS. 3 and 4 in order to make further clear the above characteristic features of the gas sensor of this invention.

Figure 3:
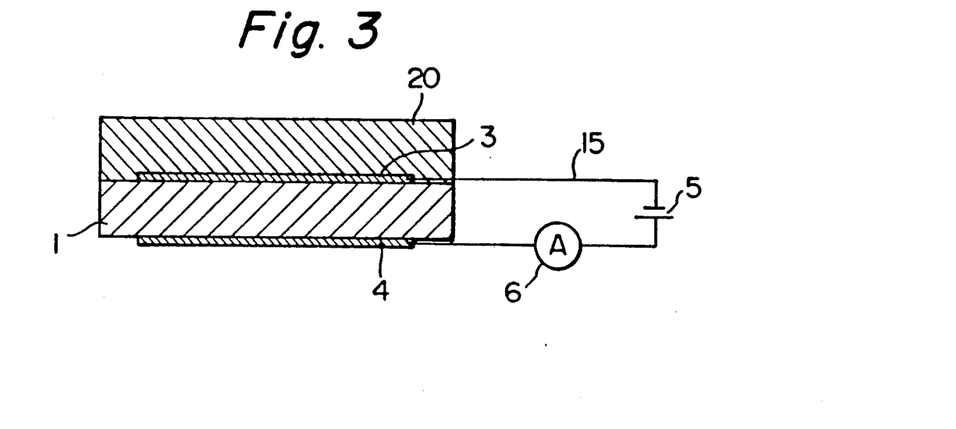
FIGS. 3 and 4 are schematic views of the conventional solid electrolyte gas sensors of a limiting current type.
Figure 4:
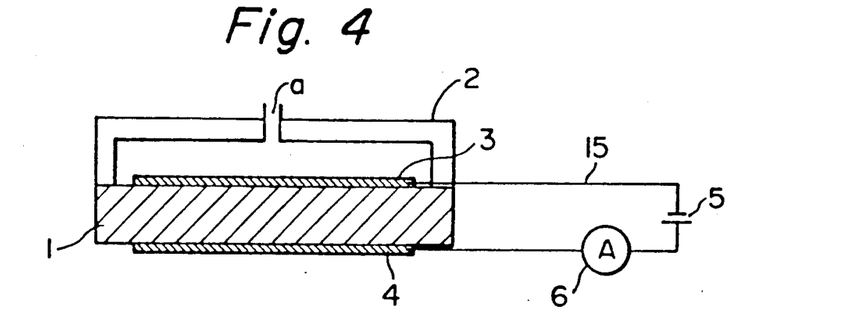

As shown in FIGS. 3 and 4, a conventional solid electrolyte gas sensor of a limiting current type has a structure in which a detection portion is formed of a solid electrolyte 1 and electrodes 3 and 4 which are disposed to sandwich the solid electrolyte 1, and a cap 2 having a capillary (in FIG. 4) or a porous ceramic 20 (in FIG. 3) is placed on one of the two electrodes so that an amount of a gas for a reaction is limited on said electrode.

In general, most of sensors of the above type have been developed to measure oxygen gas as a gas to be detected. As is described in Japanese Laid-open Patent publication No. 158344/1989, such sensors can be applied to carbon dioxide gas and other various gases such as halogen gases, $SO_2$, $SO_3$, CO, NO, $NO_2$, $NH_3$, $H_2S$, and the like. In fact, the sensor of this invention, too, can be used to measure concentrations of a variety of gases.

Meanwhile, the conventional solid electrolyte gas sensor of a limiting current type is most frequently used to measure an oxygen concentration. Therefore, an oxygen gas sensor will be specifically explained hereinbelow by reference to FIGS. 3 and 4.

In an oxygen sensor, a voltage equivalent to or higher than a voltage required for reduction of oxygen is applied between two electrodes 3 and 4 with a power source 5 such that the electrode 3 provided with a cap or a porous ceramic constitutes a cathode and the other electrode 4 constitutes an anode. On said cathode, molecular oxygen ($O_2$) is reduced to an oxygen ion ($O^{2-}$), and the oxygen ion migrates to the anode side through an ion permeation layer 1 comprising a solid electrolyte. The oxygen ion is then oxidized on the anode to form an oxygen gas, which is then discharged. An electric current occurs due to this migration of oxygen ion. This current is measurable with an ampere meter 6 connected to the power source 5 in series via a lead wire 15.

As described above, molecular oxygen fed to the cathode side is converted to an oxygen ion and drawn to the anode side. Therefore, when the amount of oxygen to be fed to the cathode is controlled by means of a diffusion resistance of a capillary of the cap 2 or pores of the porous ceramic 20, a limiting current occurs which has a constant relationship with an oxygen concentration in a gas mixture to be measured. This limiting current is measured with the above ampere meter 6. An oxygen concentration can be found on the basis of the measured limiting current and a calibration curve preliminarily prepared with regard to the relationship between an oxygen content and a limiting current value. In a standardized device, it is possible to allow such a device to directly display an oxygen concentration on the basis of a limiting current value by reference to the above calibration curve.

In such a solid electrolyte gas sensor of a limiting current type, however, it is difficult to control the size of the capillary or the porosity and diameter of pores of the porous ceramic for controlling a gas diffusion amount, which constitute a mechanism for feeding oxygen (gas to be detected) to the cathode surface. Thus, there are problems in that an output current varies to a great extent depending upon products and that a measurement value varies due to clogging, etc., in use for a long period of time.

In order to overcome the above problems, this invention does not use a method of controlling the diffusion amount and diffusion rate of a gas G by means of a cap with a capillary or a porous ceramic, but employs a method of controlling the supply amount and supply rate of a gas G contained in a gas mixture to be measured by means of a gas control screen which will be detailed later. As a result, the gas to be detected in a gas mixture measured can reach the detection portion of the sensor without any migration through pores by diffusion. Therefore, there can be obtained a sensor which is almost free from problems in variability depending upon products, variability in measurement value due to clogging, etc. in use for a long period of time, and the like.

The structure of the solid electrolyte gas sensor of this invention will be explained in detail below.

The screen (A) to control the permeation rate of a gas to be detected comprises (a1) a first solid electrolytic membrane selectively permeable to an ion derived from a specific gas to be detected and (a2) a plurality of first porous conductors being present on both front and reverse surfaces of said first solid electrolytic membrane and electrically connected to each other so as to give a potential required for oxidation and reduction of said gas to be detected.

The ion derived from a gas to be detected means an ion which the gas to be detected forms by an electrode reaction. The ion which the gas to be detected forms by an electrode reaction differs depending upon what kind of gas is to be detected.

When oxygen is a gas to be detected, the ion formed by an electrode reaction (reduction) is $O^{2-}$ as is clear in the following reaction.

$$O_2 + 4e^- \rightarrow 2O^{2-}.$$

When carbon monoxide is a gas to be detected, the electrode reaction takes place in the presence of steam, and the resultant ion is $H^-$ as is clear in the following reaction formula.

$$CO + H_2O \rightarrow CO_2 + 2H^- + 2e^-.$$

The above reaction easily proceeds at room temperature when a highly active material such as Pt black, etc., is used in an electrode (see Example 7).

When methanol is a gas to be detected, an electrode reaction takes place similarly in the presence of steam, and the resultant ion is $H^-$, as is clear in the following reaction formula.

$$CH_3OH + H_2O \rightarrow CO_2 + 6H^- + 6e^-.$$

The electrode reaction which generates an ion derived from a gas to be detected takes place under a potential applied to a plurality of the first porous conductors electrically connected to each other.

The first solid electrolytic membrane (a1) selectively permeable to an ion derived from a gas to be detected is different in material depending upon said ion. Materials therefor are known, and such materials are usable in this invention as well. When a gas to be detected is oxygen, usable as this material is a solid electrolyte prepared from a solid solution of at least one CaO, $Y_2O_3$, $Gd_2O_3$, $Sm_2O_3$, MgO, etc., in at least one of oxides such as $CeO_2$, $ZrO_2$, $HfO_2ThO_2$, $Bi_2O_3$, etc. A $CeO_2$-containing solid electrolyte is particularly preferred, since it exhibits high ionic conductivity at a low temperature and an oxygen sensor using it can be operated at a low temperature. The amount of the above dissolved solid differs depending upon a combination with the oxide which dissolves the solid. This amount is, however, in the range of 2 to 40%. When the gas to be detected is a combustible gas, known proton-conductive solid electrolytes can be used without any limitation. Examples of such protonconductive electrolytes are antimonic acid ($Sb_2O_5 \cdot nH_2O$), zirconium phosphate ($Zr(HPO_4)_2 \cdot H_2O$), phosphorus molybdate ($H_3Mo_{12}O_{40} \cdot nH_2O$), phosphorus wolframate ($H_3W_{12}O_{40} \cdot nH_2O$), uranyl phosphate ($HUO_2PO_4 \cdot nH_2O$), inorganic ion exchangers of which the typical example is H-type zeolite, polystyrene sulfonate and organic polymer ion exchangers of which the typical example is Nafion (trade name, supplied by du Pont de Nemours & Co.). The above porton-conductive solid electrolytes may be used alone or in combination. When the gas to be detected is a halogen gas, known halogen ion-conductive solid electrolytes can be used without any limitation. In case of fluorine gas, $\beta$-$PbF_2$, $CaF_2$, $SrF_2$, $LaF_2$ and $TlSn_2F_3$ can be used alone or in combination. When the gas to be detected is another halogen gas, $KAg_4I_5$, $PbCl_2$, PbBr, etc., may be used. When the gas to be detected is $SO_2$, $SO_3$, CO, $CO_2$, $NO_2$, or the like, $K_2SO_4$, $K_2CO_3$, $Ba(NO_3)_2$, etc., can be used.

The ion permeation layer formed of a solid electrolyte and used in the gas G control screen is basically required to have such a constitution that, in the detection portion, it feeds a gas (to be detected) at a lower rate than a rate of discharging the gas detected. For this reason, the solid electrolyte for use in said screen layer may be (i) a solid electrolyte having a smaller transport number than a solid electrolyte used in the detection portion, (ii) a solid electrolyte which is the same as that used in the detection position but whose effective area is decreased (e.g. to about 10 to 90%), or (iii) a solid electrolyte which is the same as that used in the detection position but whose thickness is increased. The transport number can be decreased by decreasing the ion exchange capacity of the solid electrolyte, by incorporating a metal powder having high electrical conductivity, or by some other method. On the other hand, the ion permeation layer constitutes a gas barrier and has a practical function of enduring industrial use. Therefore, the ion permeation layer has a thickness of 0.1 to 5,000 $\mu$m. In particular, when the ion permeation layer is made from an inorganic material, its thickness is preferably 0.5 to 1,000 $\mu$m, and when it is an organic material, its thickness is preferably 1 to 2,000 $\mu$m.

The ion permeation layer is produced, e.g. by a method of molding a fine powder of the above solid electrolyte, a method of molding it and sintering the molded product, a sputtering method, an ion plating method, an evaporation method, or the like. A commercially available material such as Nafion may be used as such.

Examples of the material for the porous conductors which are present on both surfaces of the ion permeation layer comprising the solid electrolyte are preferably noble metals such as platinum, palladium, rhodium, silver, etc., and oxides of these, oxides consisting of a perovskite oxides having a general formula of $La_{1-x}Sr_xBO_3$ (in which B is an element such as Co, Cu, Fe, Ni, etc., and x is a numeral of 0.01 to 0.5), and composite compositions prepared by mixing the above noble metals with metal oxides.

The porous conductors have a thickness of 0.1 to 50 $\mu$m, preferably 0.2 to 30 $\mu$m. A molecular gas or a formed ion can be efficiently diffused into the ion permeation layer since the conductors are porous.

The porous conductors can be formed on the solid electrolytic membrance by a known method, e.g. a screen printing, vacuum evaporation, chemical plating, ion plating or sputtering method. When the temperature at which the gas sensor is operated is high, the gas sensor can be heated as required. In such a case, the gas sensor may be heated by heat radiation from an external heat source or by thermal conduction or heat radiation from a heater provided to the gas sensor. In the gas sensor, the place where the heater is provided is not specially limited as far as the heater does not prevent operation of the gas sensor.

In the gas sensor of this invention, the detection portion (B) for detecting a permeation amount of ions of a gas to be detected comprises (b1) a second solid electrolytic membrane selectively permeable to an ion derived from a specific gas to be detected, (b2) a plurality of porous conductors being present on both front and reverse surfaces of the second solid electrolytic membrane and electrically connected with each other so as to give a potential required for oxidation and reduction of said gas G to be detected, and (b3) means of electrically measuring an amount of an ion derived from the gas G which permeates the second solid electrolytic membrane.

The foregoing description of the first solid electrolytic membrane (a1) and the first porous conductors (a2) in the screen (A) apply directly to the second solid electrolytic membrane (b1) and the second porous conductors (b2) in the detection portion (B).

Embodiments of the solid electrolyte gas sensor of the invention will be explained hereinafter by reference to drawings.

Figure 1:
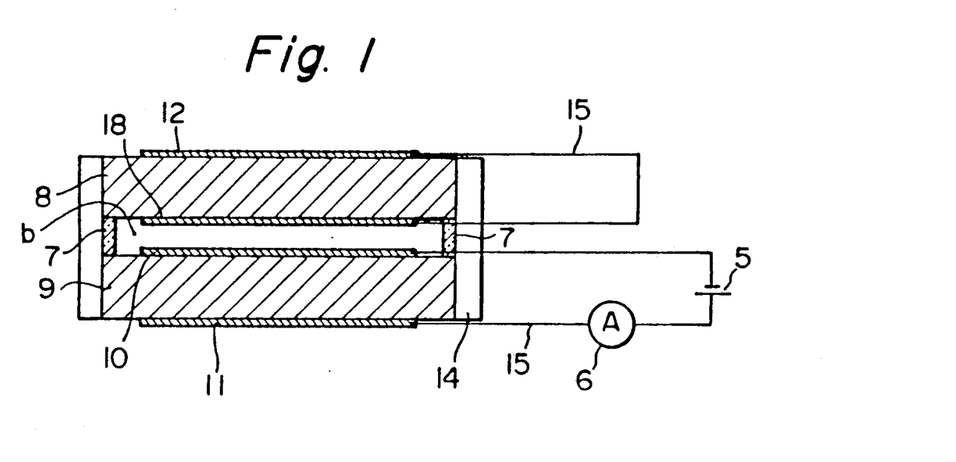
FIGS. 1 and 2 show basic structures to explain the concept of this invention.
Figure 2:
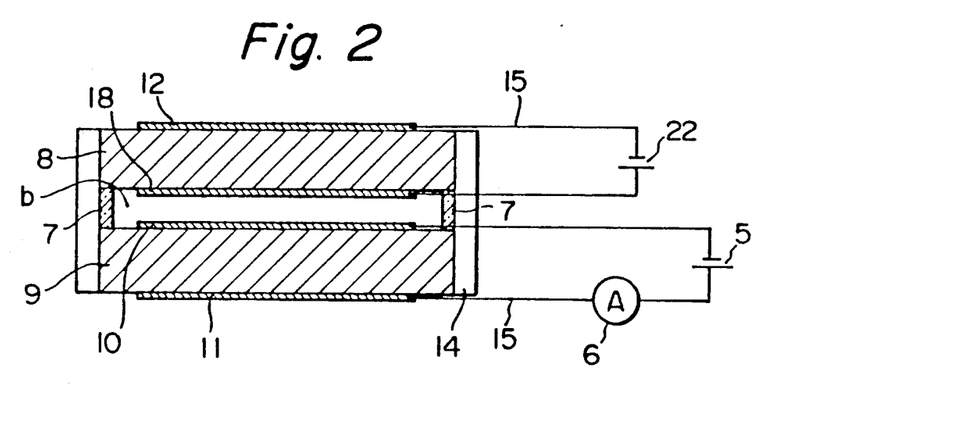

FIGS. 1 and 2 show basic structures of the gas sensor of this invention. As shown in FIGS. 1 and 2, the gas sensor of this invention has a detection portion comprising electrodes 10 and 11 and an ion permeation layer 9 formed of a solid electrolyte and placed between the electrodes 10 and 11, and a gas G control screen comprising porous conductors 12 and 18 and an ion permeation layer 8 formed of a solid electrolyte and placed between the porous conductors 12 and 18. The porous conductors 12 and 18 are electrically connected with each other. Between these two porous conductors 12 and 18, which constitute the gas G control screen, there is a potential difference sufficient to ionize a gas G contained in a gas mixture to be measured or generate an ion by an electrode reaction of the gas G. When the gas G is oxygen, etc., such a potential difference is provided by an electromotive force of a concentration cell formed due to a concentration difference in the gas G with which each of the conductors 12 and 18 is in contact. Depending upon gases to be detected, however, an oxidation or reduction potential to generate ions is sometimes large, or an overpotential between the gas G and the porous conductor 12 is sometimes also large. In such a case, it is required to apply a suitable voltage with an external power source 22 as shown in FIG. 2. The detection portion of the sensor has the same mechanism as that of a conventional solid electrolyte gas sensor of a limiting current type. That is, the detection portion comprises porous electrodes 10 and 11 and an ion permeation layer 9 placed between the porous electrodes 10 and 11, and these two electrodes 10 and 11 are connected with each other through a power source 5 and an ampere meter 6 in series via a lead wire 15 to form a circuit. The gas G control screen and the detection portion are gastightly sealed with a sealing member 7 in their peripheries. The material for the sealing member 7 is not specially limited if it is impermeable to a gas to be detected, e.g. oxygen. As a sealing member, glass, inorganic cement, a ceramic having a low melting point, etc., are usable. Of these materials, it is preferred to use those which have a thermal expansion coefficient equivalent to or slightly lower than that of the ion permeation layer. Further, in view of junction, it is preferred to use those which are fine particles having a diameter of not more than 10 $\mu$m, preferably not more than 5 $\mu$m. Furthermore, it is industrially advantageous to form a casing 14 by coating outer side surfaces of the gas control screen and the detection portion with a sealing material in order to improve gastightness and protect the outer surfaces.

This invention has its characteristic features in use of two ion permeation layers 8 and 9 which are formed of a solid electrolyte, and known solid electrolytes can be used, as described above, if they are permeable to intended ions.

Figure 5:
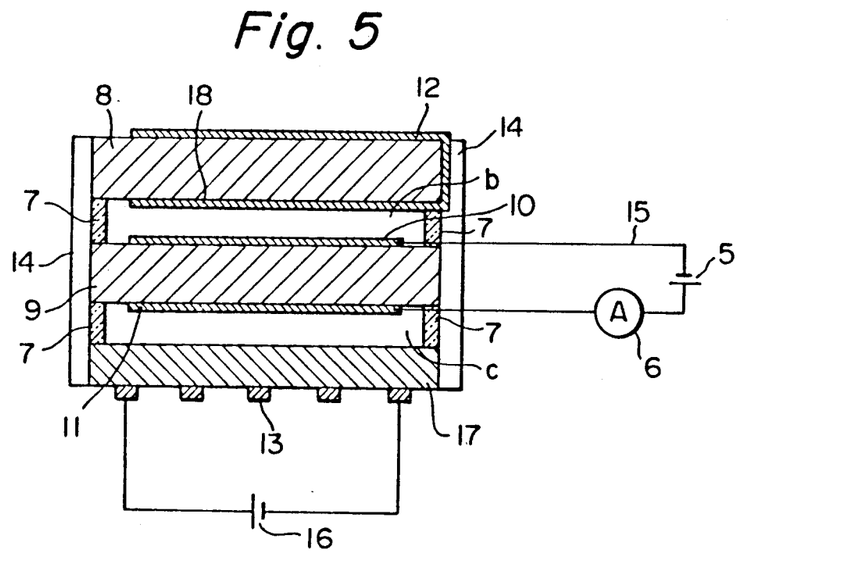
FIGS. 5 to 11 respectively show embodiments of the solid electrolyte gas sensor of a limiting current type according to this invention.

FIG. 5 shows a specific embodiment of the gas sensor of this invention, in which porous conductors 12 and 18 of a gas G control screen are connected at one end, and an electromotive force in said screen portion is produced by a difference between a concentration of a gas G in contact with the conductor 12 and a concentration of a gas G in contact with the conductor 18. Said screen and a detection portion are sealed in their peripheries with a sealing member 7 to form a space b. Further, the detection portion of the sensor is provided with a space c in its lower portion, and further provided with an electrically insulating porous element 17, a heater 13 and a power source 16 for said heater. The embodiment in FIG. 5 is also constituted such that the amount of a gas to be fed to the space b through a solid electrolytic membrane 8 is smaller than the amount of a gas to be drawn into the space c. The electrically insulating porous element 17 has pores whose diameter and number are sufficient to discharge a gas, drawn into the space c, without any resistance.

Figure 6:
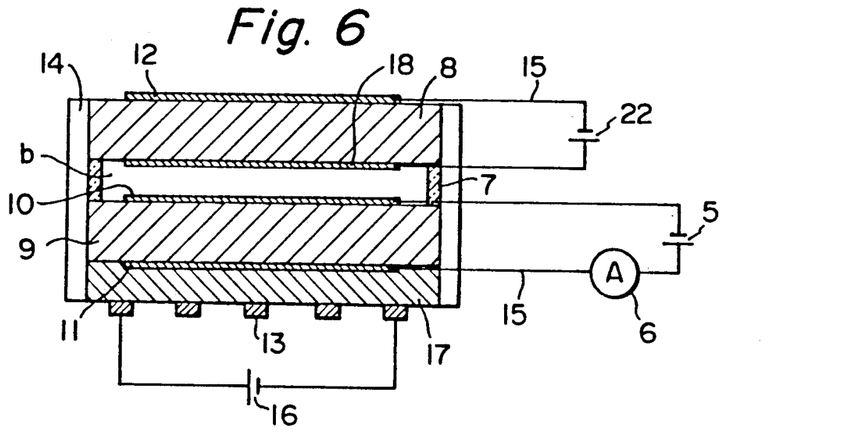

FIG. 6 shows another embodiment, in which a voltage equivalent to or higher than a voltage required to produce an electrode reaction of a gas G contained in a gas mixture measured on a surface of a conductor 12 is charged between the conductor 12 and a conductor 18 in a gas G control screen with an external power source 22. Further, this embodiment has a constitution in which a porous element 17 and an electrode 11 are brought into intimate contact for heating efficiency.

Figure 7:
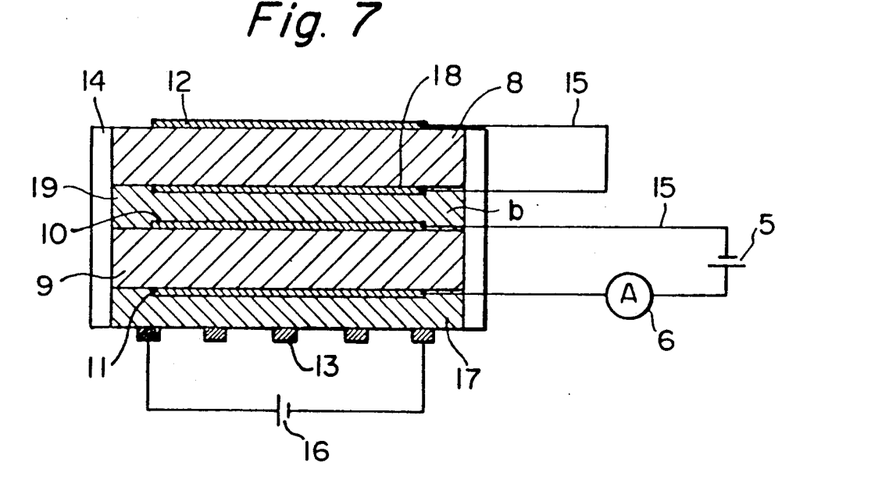

FIG. 7 shows another embodiment in which a spacer 19 formed of a porous substance is placed in a space b existent between a gas G control screen and a detection portion. The material for the spacer is not specially limited as far as it does not limit permeation of a gas to be detected. Generally preferred are porous ceramics such as $SiO_2.MgO$, $SiO_2.Al_2O_3$, zeolite and $SiO_2$. These porous ceramics may be freely selected as far as they do not limit permeation of a gas to be detected.

Figure 8:
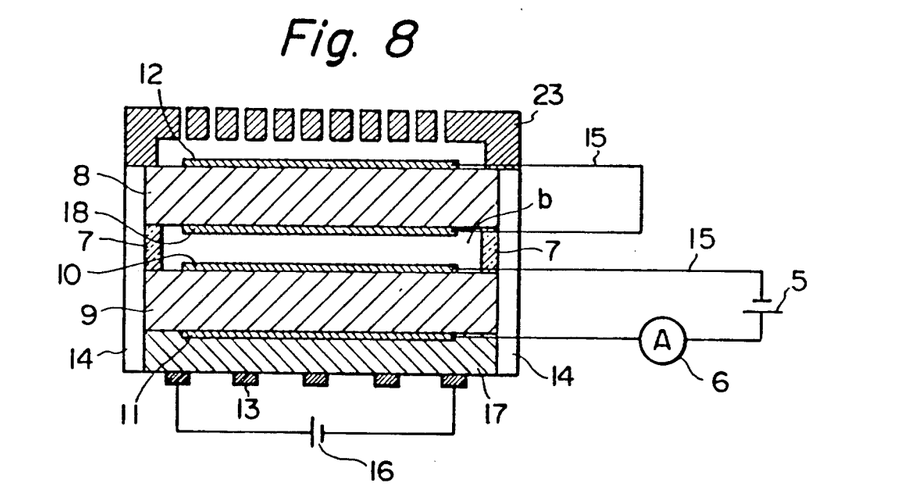

FIG. 8 shows an embodiment in which a cover 23 formed of a wire net, a ceramic having a high opening ratio or other porous substance is provided in order to protect a conductor 12 which is to be in contact with a gas mixture to be measured.

Figure 9:
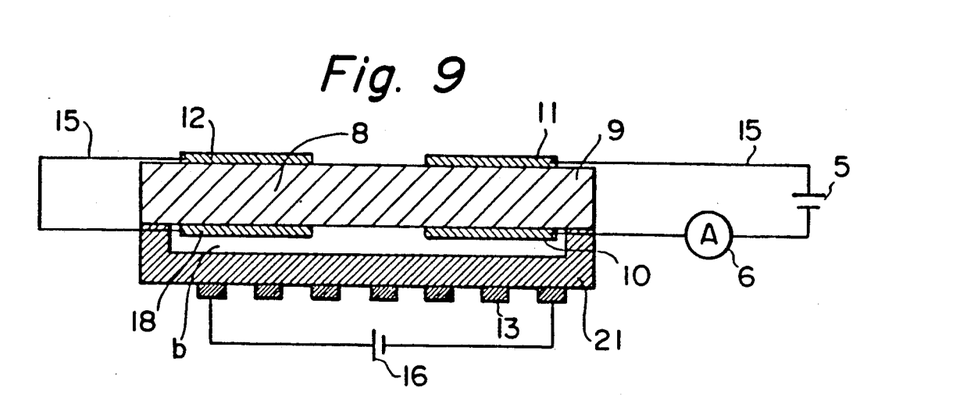

FIG. 9 shows another embodiment in which a gas G control screen covers a detection portion, and a solid electrolytic membrane 8 of the gas G control screen and a solid electrolytic membrane 9 of a detection portion are formed as a unitary structure. A gas fed through said screen is retained in a space b formed with a cover 21, and then fed to the detection portion. That is, an ion formed by an electrode reaction on a conductor 12 of the gas G control screen is converted to a molecular gas with a conductor 18 and fed to the space b. This molecular gas in the space b is then drawn in the detection portion, and discharged through an electrode 11. This embodiment has characteristic features in that due to a heater 13 positioned on a lower surface, the gas G control screen and the detection portion of the sensor can be uniformly heated.

Figure 10:
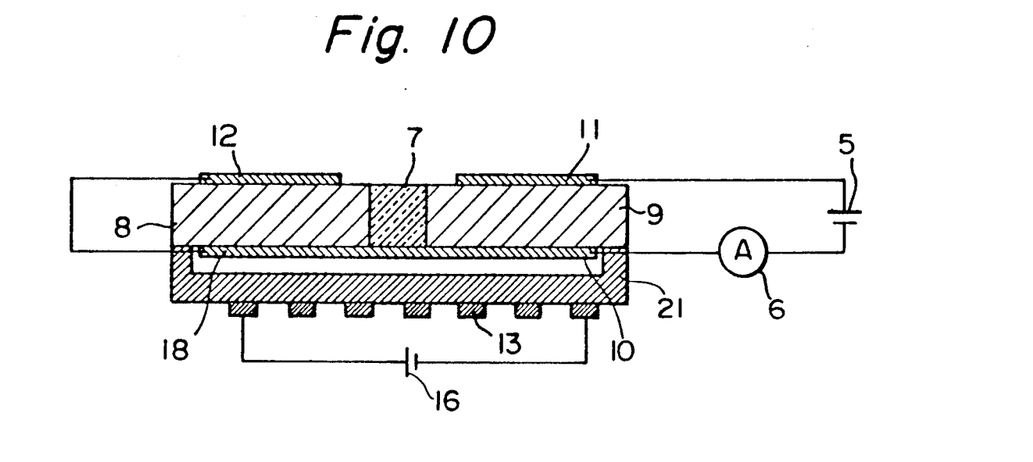

FIG. 10 shows a variant of the embodiment shown in FIG. 9. A solid electrolytic membrane 8 and a solid electrolytic membrane 9 are isolated with an insulating sealing member 7, and a conductor 18 of a gas G control screen and an electrode 10 of a detection portion are integrally constituted. In this embodiment, the conductor 18 and the electrode 10 have the same potential. As can be understood, however, the measurement is possible without any problem by retaining a potential difference between a conductor 12 and the conductor 18 and a potential difference between the electrode 10 and an electrode 11 in a range required for an electrode reaction of a gas formed from the ion which is derived from the gas G.

Figure 11:
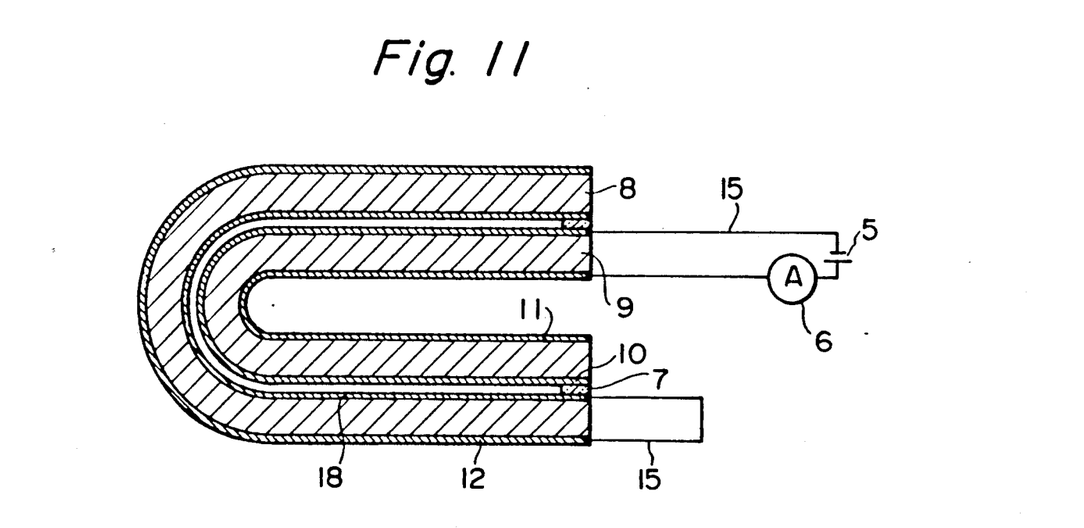

FIG. 11 shows a variant which is basically the same as the embodiment shown in FIG. 1. The structure of the sensor of this invention shall not be limited to a plate-form, and for example, it can be cylindrical as shown in FIG. 11.

As can be understood from the above explanation, this invention shall not be limited to the above embodiments, but includes any embodiment which is a solid electrolyte gas sensor of a limiting current type and employs a process in which a gas to be fed to the detection portion permeates the ion permeation layer formed of the solid electrolytic membrane as an ion and then fed again.

According to this invention, therefore, on the basis of the above basic principle of the solid electrolyte gas sensor of this invention, there is also provided a method of measuring a concentration of a gas to be detected in a gas mixture, which comprises:

(1) feeding a gas mixture containing a gas to be detected onto one of a plurality of first porous conductors of a screen for control of a permeation rate of the gas to be detected, thereby to allow the gas to pass through the screen, said screen comprising:
  (a1) a first solid electrolytic membrane, which is selectively permeable to ions derived from a specific gas to be detected, and
  (a2) a plurality of the first porous conductors, which are present on both front and reverse surfaces of said first solid electrolytic membrane and electrically connected with each other so as to give a potential required for oxidation and reduction of said gas to be detected, (2) feeding said gas, which has passed the screen, onto one of a plurality of second porous conductors of a detection portion for detecting a permeation amount of ions of the gas to be detected thereby to allow the gas to pass through a second solid electrolytic membrane and a plurality of the second porous conductors at a higher rate than the gas is fed; the detection portion comprising,
  (b1) the second solid electrolytic membrane, which is selectively permeable to ions derived from a specific gas to be detected,
  (b2) a plurality of the second porous conductors, which are present on both front and reverse surfaces of said second solid electrolytic membrane and electrically connected with each other so as to give a potential required for oxidation and reduction of said gas to be detected, and
  (b3) means of electrically measuring an amount of ions derived from the gas to be detected which permeates the second solid electrolytic membrane; and (3) detecting an amount of the gas to be detected which has passed at the above step (2) with the above means (b3).

This invention will be explained further in detail by reference to Examples, which however shall not limit this invention.

Limiting current properties of gas sensors in Examples were measured according to the following method.

A gas sensor was placed in a gas mixture containing a different concentration of a gas to be detected, and a D.C. voltage was applied to electrodes of a detection portion. The applied voltage was continuously changed at a rate of 0.04 V/min., and currents occurred were measured with an ampere meter and recorded in a recorder. On the basis of the results obtained, voltages at which a limiting current was commonly obtained in the concentration of a gas to be detected were regarded an optimum applied voltage.

EXAMPLE 1

(1) As shown in FIG. 5, an oxygen sensor was constituted of an oxygen detection portion in which electrodes (of a porous conductor) 10 and 11 were formed on both the surfaces of an ion-permeable layer (solid electrolytic membrane) 9, an oxygen control screen in which porous conductors 12 and 18 formed on both surfaces of an ion-permeable layer (solid electrolytic membrane) 8 were electrically connected to each other, and a heater portion in which a heater 13 was formed on a porous ceramic 17. The oxygen detection portion, the oxygen control screen and the heater portion were bonded with a glass 7, and externally sealed with a glass 14. A direct current voltage 16 was applied to the heater 13 of the heater portion to heat an oxygen sensor element to 450° C. A direct current voltage 5 was applied so that in the oxygen detection portion the electrode 10 on the side of the oxygen control screen constituted a cathode and the electrode 11 on the heater portion side constituted an anode. Further, an ampere meter 6 was connected to a power source in series to measure an occurring current.

In the above structure, as the ion-permeable layers 8 and 9, there were used dense disk-formed solid electrolyte sintered members having a diameter of 4 mm and a thickness of about 0.3 mm, which were prepared by molding a $(CeO_2)_{0.7}(CaO)_{0.3}$ powder of a solid solution of 30 mol % of calcium oxide in oxygen ion-conducting cerium oxide and sintering the resultant molded material.

The electrodes 10 and 11 were those which were prepared by screen-printing a platinum paste and baking the resultant printed plates at 800° C. And a platinum wire was used as a lead wire 15. Further, the porous conductors 12 and 18 of the oxygen control screen were those which were prepared by screen-printing a platinum paste on both surfaces of the ion-permeable layer 8, partly connecting the resultant printed layers along an end surface of the ion-permeable layer 8 with a platinum paste, and baking the resultant plate at 800° C.

The porous ceramic 17 used in the heater portion was a disk-formed sintered material having a diameter of 4 mm and a thickness of about 0.6 mm, which was a heat-resistant inorganic material having sufficient pores to prevent oxygen diffusion from rate-controlling and a thermal expansion coefficient nearly equivalent to that of the ion-permeable layer, and which was prepared by molding an $MgO \cdot SiO_2$ powder into a disk and sintering it.

As the heater 13, known materials are suitably usable. In view of stability and heat resistance, the heater 13 used in this Example is that which was prepared by screen-printing a platinum paste on the above porous ceramic to form a corrugated layer and baking it at 900° C.

As the bonding glass 7, preferably usuable are those having a thermal expansion coefficient equivalent to or slightly smaller than that of the ion-permeable layer and a particle diameter of not more than 10 μm, preferably not more than 5μ. In this Example, therefore, a glass powder having an average diameter of 6 μm was milled with a ball mill for 3 hours, and the milled glass powder was formed into a paste by adding terepineol and ethyl cellulose. Then, the oxygen detection portion, the heater portion and the oxygen control screen were bonded by screen-printing the paste on those portions of the ion-permeable layer 9 on which the electrodes were not formed. The glass 14 used for the sealing was formed by applying the same glass paste as above to the outer surface of the oxygen sensor element twice. These glass members 7 and 14 were densified by sintering them at 620° C. so that oxygen did not permeate therethrough.

Figure 12:
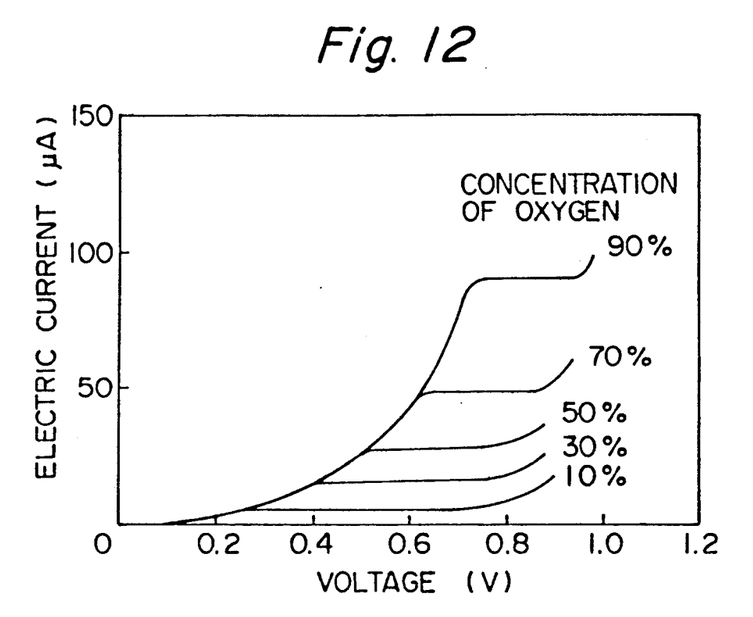
FIG. 12 shows a relationship between a voltage and an electric current with regard to various oxygen concentrations in a gas mixture measured in an oxygen sensor in Example 1.

(2) The above sensor was placed in a gas mixture to be measured which contains a different oxygen concentration, and a current was measured by changing voltages to be applied between the electrodes 10 and 11. FIG. 12 shows the results, in which the ordinate axis indicates currents (μA) and the abscissa axis indicates voltages (V). In FIG. 12, with regard to all of oxygen concentrations, there are observed portions showing no change in current while the voltage was changed, i.e. portions of lines nearly parallel with the abscissa axis. These linear portions individually show limiting current values in corresponding oxygen concentrations.

FIG. 12 shows that 800 mV is a voltage with which the limiting current values are obtained commonly with regard to all of the oxygen contents. Table 1 shows the relationship between the limiting current value and the oxygen concentration at the 800 mV.

TABLE 1

| | Oxygen concentration (%) | | | | | | | |
|---|---|---|---|---|---|---|---|---|
| | 5 | 10 | 21 | 30 | 50 | 70 | 80 | 90 |
| Limiting current (μA) | 8.3 | 9.5 | 13.4 | 17.5 | 29.2 | 45.6 | 58.5 | 79.3 |

Figure 13:
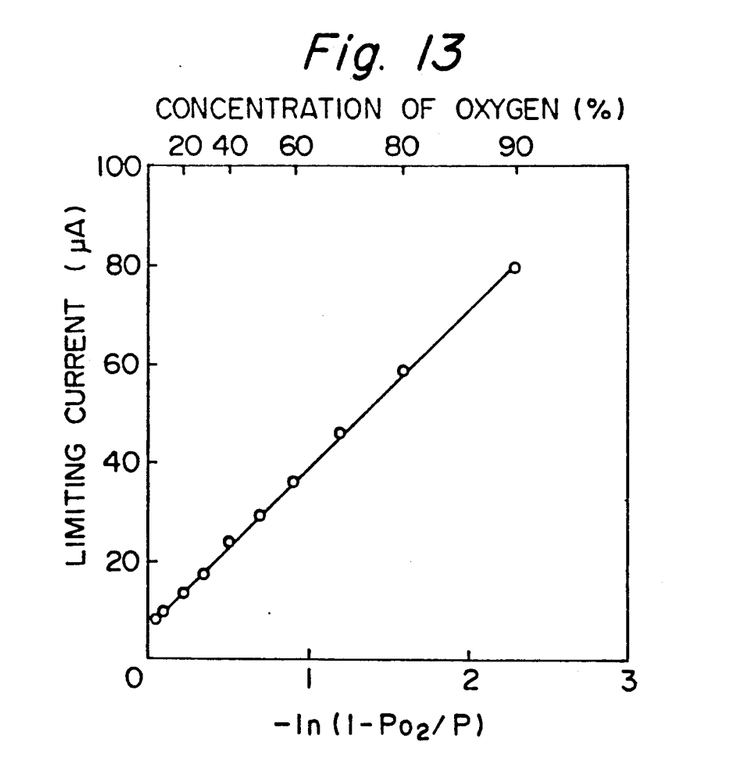
FIGS. 13 to 15 show relationships between limiting current values ($\mu A$) and oxygen concentrations $[-\ln(1-PO_2/P)$ in which $PO_2$ denotes a partial pressure of a gas G (oxygen) contained in a gas mixture measured, and P denotes a total pressure] in Examples 1, 7 and 8.

The relationship shown in Table 1 is illustrated in FIG. 13, in which the ordinate axis indicates limiting current values (μA), the abscissa axis on the bottom indicates a function of oxygen concentration $-\ln(1-PO_2/P)$ in which P is a total pressure of a gas measured and $PO_2$ is an oxygen partial pressure, and the abscissa axis on the top indicates oxygen concentrations (%).

FIG. 13 is used as a calibration curve to determine an oxygen concentration in a gas mixture of which the oxygen concentration is unknown. That is, a gas mixture is measured with an oxygen sensor shown in FIG. 5 for a limiting current value, and the oxygen concentration in the gas mixture is determined on the basis of the limiting current value by reference to the above calibration curve.

(3) Further, thirty oxygen sensors were prepared in the same way as in the preparation of the above oxygen sensor, and a degree of variability of outputted current among these oxygen sensors were determined. That is, an optimum voltage obtained by measurement of limiting current characteristics was applied to each of the oxygen sensors, and output currents in atmosphere were measured. Table 2 shows a maximum value, average value and variability coefficient of outputted currents. Table 2 shows that the oxygen sensor of this invention exhibits a smaller variability in outputted current than a conventional oxygen sensor having pores or a porous ceramic, and can be produced with good reproductiveness.

(4) Further, in order to determine withstandability to clogging, thirty oxygen sensors were placed in a gas exhausted from a heavy oil-fed boiler, and outputted currents were measured by applying thereto an optimum voltage obtained by measurement of limiting current characteristics. Table 3 shows numbers of those oxygen sensors whose output currents were reduced to not more than ½ of the initial output current after 3, 5, 10, 20 and 30 days. Table 3 shows that the oxygen sensor of this invention is almost free from a decrease in output current, which is caused by the clogging in atmosphere full of dust and soot such as a gas exhausted from a heavy oil-fed boiler as compared with a conventional oxygen sensor having pores or a porous ceramic, or that the oxygen sensor of this invention exhibits a stable output for a long period of time.

EXAMPLE 2

(1) An oxygen sensor as shown in FIG. 7 was produced. This oxygen sensor was a variant from the oxygen sensor shown in FIG. 5. That is, the oxygen detection portion and the oxygen control screen were bonded with a ceramic paste in stead of the glass 7, and a porous insulating ceramic 19 was present in a space b between the oxygen detection portion and the oxygen control screen. Further, in this oxygen sensor, a heater 13 was formed on a porous ceramic 17 formed by screen-printing a ceramic paste on that side which was opposite to the side of the oxygen control screen of the oxygen detection portion. The above porous ceramics 17 and 19 had a porosity sufficient to prevent oxygen permeation from rate controlling.

(2) This oxygen sensor also gave a limiting current value having a constant relationship with oxygen concentrations in a gas mixture to be measured in the same way as in Example 1.

Further, oxygen sensors produced in the same way as above were measured for a variability in outputted currents in the same way as in Example 1, and Table 2 shows the results, in which the variability in outputted current among the oxygen sensors of Example 2 of this invention was as small as that of the sensors in Example 1 as compared with a conventional oxygen sensors having pores or a porous ceramic. Furthermore, the sensor of this invention can be produced with good reproductiveness.

Further, the withstandability to clogging was measured in the same way as in Example 1, and the results are shown in Table 3. Table 3 shows that the oxygen sensor of this Example 2 is almost free from a decrease in output current caused by the clogging differently from a conventional oxygen sensor having pores or a porous ceramic, and that the oxygen sensor of this invention exhibits a stable output for a long period of time.

EXAMPLE 3

(1) An oxygen sensor element as shown in FIG. 8 was produced. This sensor had almost the same structure as that of the sensor shown in FIG. 5. The difference is that this sensor was provided with a protective cover 23 to prevent accumulation of dust and soot on a porous conductor layer 12 directly exposed to a gas mixture. As the above porous conductor layer 12, those which do not limit permeation of oxygen current are usable without any limitation. In general, preferred are porous ceramics such as $SiO_2 \cdot MgO$, $SiO_2 \cdot Al_2O_3$, $SiO_2$ and zeolite, metal meshes such as stainless steel, and ceramic asbestos such as asbestos.

(2) This oxygen sensor also gave a limiting current value having a constant relationship with oxygen concentrations in a gas mixture to be measured in the same way as in Example 1.

Further, oxygen sensors produced in the same way as above were measured for a variability in outputted currents in the same way as in Example 1, and Table 2 shows the results, in which the variability in outputted currents among the oxygen sensors of Example 3 of this invention was as small as those of the sensors in the foregoing Examples as compared with a conventional oxygen sensor having pores or a porous ceramic. And, the sensor of this invention can be produced with good reproductiveness.

Further, the withstandability to clogging was measured in the same way as in Example 1, and the results are shown in Table 3. Table 3 shows that the oxygen sensor of this Example 3 is almost free from a decrease in output current caused by the clogging differently from a conventional oxygen sensor having pores or a porous ceramic, or that the oxygen sensor of this invention exhibits a stable output for a long period of time.

EXAMPLE 4

(1) An oxygen sensor element as shown in FIG. 9 was produced. This sensor had an oxygen ion permeable layer 8 which was prepared in the same way as in Example 1 from the same material as the sintered material used in Example 1 except that it had a rectangular parallelepiped shape having a length of about 4 mm, a width of about 3 mm and a thickness of about 0.6 mm. Porous conductor layers 11 and 12 were formed on one surface of the oxygen ion permeable layer 8, and porous conductor layers 10 and 18 were similarly formed on the other surface thereof. A dense ceramic 21 was bonded to the side of the conductor layers 10 and 18, and a heater 13 was formed thereon.

The conductors 12 and 18 were also short-circuited with a lead wire 15. On the other hand, a direct voltage 5 was applied between the conductors 10 and 11, and an ampere meter was also present.

(2) The above sensor also gave a limiting current value having a constant relationship with oxygen concentrations in a gas mixture to be measured in the same way as in Example 1.

Further, oxygen sensors produced in the same way as above were measured for a variability in outputted currents in the same way as in Example 1, and Table 2 shows the results, in which the variability in outputted currents among the oxygen sensors of Example 4 of this invention was as small as those among the sensors of the foregoing Examples as compared with a conventional oxygen sensor having pores or a porous ceramic. And, the sensor of this invention can be produced with good reproductiveness.

Further, the withstandability to clogging was measured in the same way as in Example 1, and the results are shown in Table 3. Table 3 shows that the oxygen sensor of this Example 4 is almost free from a decrease in output current caused by the clogging differently from a conventional oxygen sensor having pores or a porous ceramic, and that the oxygen sensor of this invention exhibits a stable output for a long period of time.

EXAMPLE 5

(1) An oxygen sensor element as shown in FIG. 10 was produced. In this sensor, there were used two oxygen ion permeable layers which were the same as the oxygen ion permeable layer in Example 4. A porous conductor layer 12 was formed on one surface of the oxygen ion permeable layer 8, and a porous conductor layer 11 was formed on one surface of the oxygen ion permeable layer 9. The oxygen permeable layers 8 and 9 were placed such that the surfaces, on which the conductor layers 11 and 12 had been formed, faced upward, and were electrically insulated from each other by bonding them end to end with a glass 7. Then, porous conductor layers 10 and 18 were formed on the other surfaces, on which the conductor layers 11 and 12 had not been formed, integrally as a common continuous layer. Then, a dense ceramic 21 was bonded to the side on which this continuous layer was formed, and a heater 13 was formed thereon. The conductor layer 12 and the continuous layer were short-circuited with a lead wire, and a direct voltage 5 was applied between the conductor 11 and the continuous layer. An ampere meter 6 was used as shown in FIG. 10.

(2) The above sensor also gave a limiting current value having a constant relationship with oxygen concentrations in a gas mixture to be measured in the same way as in Example 1.

Further, oxygen sensors produced in the same way as above were measured for a variability in outputted currents in the same way as in Example 1, and Table 2 shows the results, in which the variability in outputted current among the oxygen sensors of Example 5 of this invention was as small as those among the sensors of the foregoing Examples as compared with a conventional oxygen sensor having pores or a porous ceramic. And the sensor of this invention can be produced with good reproductiveness.

Further, the withstandability to clogging was measured in the same way as in Example 1, and the results are shown in Table 3. Table 3 shows that the oxygen sensor of this Example 5 is almost free from a decrease in output current caused by the clogging differently from a conventional oxygen sensor having pores or a porous ceramic, and that the oxygen sensor of this invention exhibits a stable output for a long period of time.

EXAMPLE 6

(1) An oxygen sensor element as shown in FIG. 11 was produced. This sensor was produced by preparing an oxygen control screen, which was formed of a cylindrical ion permeable layer 8 and porous conductor layers 12 and 18 formed on surfaces of the ion permeable layer 8, and bonding an oxygen sensor portion, which was formed of an ion pemeation layer 9 having the same form as, and being smaller than, the ion permeable layer 8 and an electrode 11 formed on surfaces of the ion permeable layer 9, to the oxygen control screen with a glass 7 such that the oxygen sensor portion was positioned within the oxygen control screen. In FIG. 11, the oxygen control screen was positioned outside and the oxygen sensor portion was positioned inside. When this structure is reverse, i.e. when the oxygen sensor portion is positioned outside with oxygen control screen inside, a necessary voltage is to be applied to the oxygen sensor portion such that an electrode on that side of the oxygen sensor portion which is in contact with the oxygen control screen constitutes a cathode and that on the reverse side constitutes an anode.

(2) The above sensor also gave a limiting current value having a constant relationship with oxygen concentrations in a gas mixture to be measured in the same way as in Example 1.

Further, oxygen sensors produced in the same way as above were measured for a variability in outputted currents in the same way as in Example 1, and Table 2 shows the results, in which the variability in outputted current among the oxygen sensors of Example 6 of this invention was as small as those among the sensors of the foregoing Examples as compared with a conventional oxygen sensor having pores or a porous ceramic. And the sensor of this invention can be produced with good reproductiveness.

Further, the withstandability to clogging was measured in the same way as in Example 1, and the results are shown in Table 3. Table 3 shows that the oxygen sensor of this Example 6 is almost free from a decrease in output current caused by the clogging differently from a conventional oxygen sensor having pores or a porous ceramic, and that the oxygen sensor of this invention exhibits a stable output for a long period of time.

TABLE 2

|  | Current ($\mu A$) | | | Variation coefficient |
|---|---|---|---|---|
|  | Average | Minimum | Maximum |  |
| Example 1 | 13.8 | 12.4 | 15.1 | 5.4 |
| Example 2 | 14.6 | 11.7 | 16.0 | 6.1 |
| Example 3 | 23.4 | 20.1 | 25.7 | 5.7 |
| Example 4 | 30.5 | 25.4 | 36.1 | 5.8 |
| Example 5 | 25.3 | 20.6 | 32.6 | 6.0 |
| Example 6 | 56.2 | 43.8 | 68.3 | 6.3 |
| Sensor with pores | 220 | 138 | 293 | 24.8 |
| Sensor with porous ceramic | 128 | 45 | 240 | 43.6 |

TABLE 3

|  | 3 days | 5 days | 10 days | 20 days | 30 days | Total |
|---|---|---|---|---|---|---|
| Example 1 | 0 | 0 | 1 | 2 | 1 | 4 |
| Example 2 | 0 | 1 | 2 | 1 | 3 | 6 |
| Example 3 | 0 | 0 | 2 | 2 | 2 | 6 |
| Example 4 | 1 | 1 | 1 | 3 | 2 | 8 |
| Example 5 | 0 | 0 | 2 | 1 | 2 | 5 |
| Example 6 | 1 | 2 | 1 | 2 | 1 | 7 |
| Sensor with pores | 4 | 5 | 10 | 4 | 2 | 25 |
| Sensor with porous ceramic | 1 | 3 | 5 | 5 | 6 | 20 |

EXAMPLE 7

(1) An oxygen sensor element having a structure as shown in FIG. 5 was produced in the same way as in Example 1 except for the following: A sintered body of a solid solution of 7 mol % of yttrium oxide in oxygen ion-conducting zirconium oxide $(ZrO_2)_{0.93}(Y_2O_3)_{0.07}$ was used as ion permeable layers 8 and 9. Platinum was used as porous electrodes 10 and 11 and porous conductor layers 12 and 18. The same heater and the same glass as those in Example 1 were used as a heater 13 and glass members 7 and 14.

A direct current voltage was applied to the heater 13 to heat the element to 500° C. A direct current voltage was applied such that the electrode 10 constituted a cathode and the electrode 11 constituted an anode in the same way as in Example 1, and the resultant current was measured with an ampere meter 6.

(2) As a result, limiting current values as shown in FIG. 12 were obtained with regard to all oxygen concentrations.

Table 4 shows the relationship between a limiting current value and an oxygen concentration at a voltage of 1.3 V at which the limiting currents were obtained commonly with all oxygen concentrations.

TABLE 4

|  | Oxygen concentration (%) | | | | | | | |
|---|---|---|---|---|---|---|---|---|
|  | 5 | 10 | 21 | 30 | 50 | 70 | 80 | 90 |
| Limiting current | 17 | 28 | 50 | 87 | 179 | 340 | 437 | 615 |

TABLE 4-continued

| | Oxygen concentration (%) | | | | | | |
|---|---|---|---|---|---|---|---|
| | 5 | 10 | 21 | 30 | 50 | 70 | 80 | 90 |
| (μA) | | | | | | | | |

Figure 14:
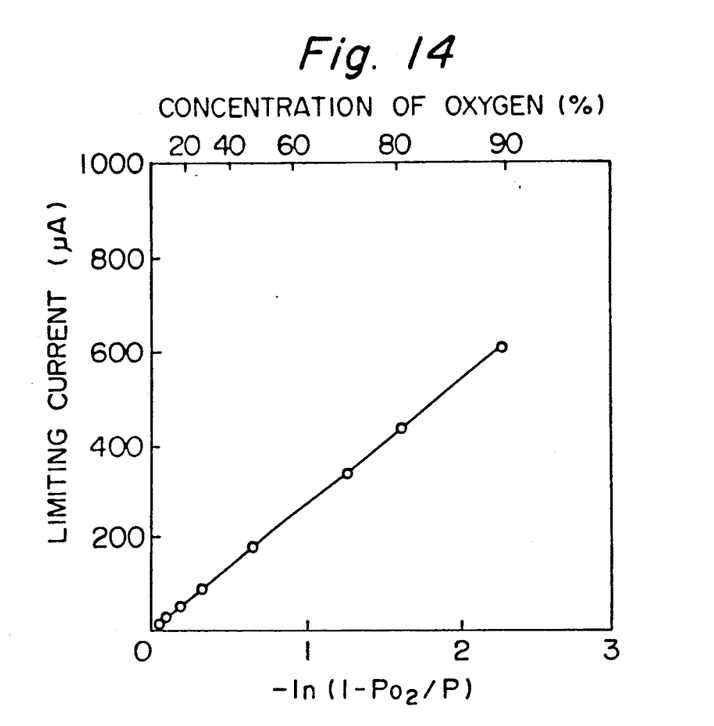

The relationship shown in Table 4 is illustrated in FIG. 14, in which the ordinate axis indicates limiting current values (μA), the abscissa axis on the bottom indicates a function of oxygen concentration $-\ln(1-PO_2/P)$, and the abscissa axis on the top indicates oxygen concentrations (%). This element using $(ZrO_2)_{0.93}(Y_2O_3)_{0.07}$ as an ion permeable layer was an embodiment of which the element temperature was higher than that of the element using $(CeO_2)_{0.73}\cdot(CaO)_{0.3}$. This sensor element exhibited large limiting current values and gave a calibration curve as shown in FIG. 14.

EXAMPLE 8

(1) An oxygen sensor element having a structure as shown in FIG. 5 was produced in the same way as in Example 1 except for the following: A composite material of $La_{0.6}Sr_{0.4}CoO_3$, which was perovskite-type oxide, with platinum was used as porous electrodes 10 and 11 and porous conductor layers 12 and 18, a sintered material of $(CeO_2)_{0.7}(CaO)_{0.3}$ was used as ion permeable layers 8 and 9, and the same heater and the same glass as those in Example 1 were used as a heater 13 and glass members 7 and 14.

The composite material used for the electrodes 10 and 11 and the conductor layers 12 and 18 was a paste prepared by mixing lanthanum carbonate, strontium carbonate and cobalt acetate in a predetermined ratio, firing the resultant mixture, milling the resultant fired product to form a powder of perovskite-type oxide $La_{0.6}Sr_{0.4}CoO_3$, and mixing this powder with a platinum paste at a weight ratio of 2:8, and the electrodes 10 and 11 and the conductor layers 12 and 18 were formed by screen-printing the above paste.

A direct current voltage was applied to the heater 13 to heat the element to 400° C. A direct current voltage was applied such that the electrode 10 constituted a cathode and the electrode 11 constituted an anode in the same way as in Example 1, and the resultant current was measured with an ampere meter 6.

(2) As a result, limiting current values as shown in FIG. 12 were obtained with regard to all oxygen concentrations.

Table 4 shows the relationship between a limiting current value and an oxygen concentration at a voltage of 1.0 V at which the limiting currents were obtained commonly with all oxygen concentrations.

TABLE 5

| | Oxygen concentration (%) | | | | | | | |
|---|---|---|---|---|---|---|---|---|
| | 5 | 10 | 21 | 30 | 50 | 70 | 80 | 90 |
| Limiting current (μA) | 11 | 17 | 38 | 61 | 123 | 231 | 271 | 382 |

Figure 15:
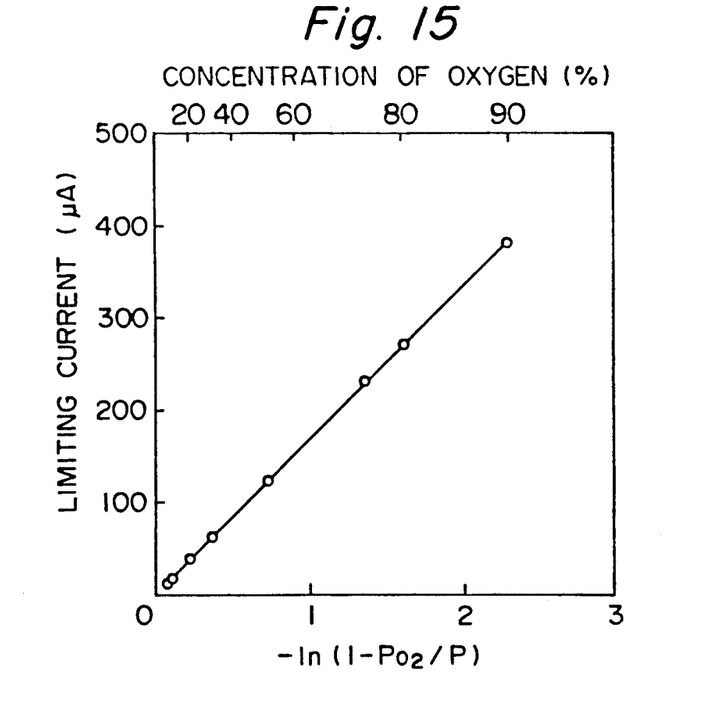

The relationship shown in Table 5 is illustrated in FIG. 15, in which the ordinate axis indicates limiting current values (μA), the abscissa axis on the bottom indicates a function of oxygen concentration $-\ln(1-PO_2/P)$, and the abscissa axis on the top indicates oxygen concentrations (%). This element using the composite material as the electrodes exhibited large limiting current values in spite of a low element temperature, and gave a calibration curve as shown in FIG. 15.

EXAMPLE 9

A hydrogen sensor having a structure shown in FIG. 1 was produced. A mixture of proton-conducting antimonic acid $(Sb_2O_5\cdot H_2O)$ with a Teflon powder was used as ion permeable layers 8 and 9. Porous electrodes 10 and 11 and porous conductor layers 12 and 18 were formed by molding platinum black concurrently with molding the proton conductor into disks having a diameter of 5 mm. The ion permeable layers 8 and 9 formed in such a manner that the ion permeable layer 8 had a greater thickness than the ion permeable layer 9 in order to differentiate an ion permeation amount per unit time. A detection portion and an ion permeable layer were bonded with a glass 7 and the end portion thereof was sealed with a glass 14 in the same way as in Example 1. The glass members 7 and 14 were so densified as to prevent gas permeation by sintering them at 250° C.

(2) In this sensor, a direct current voltage 5 was applied such that the electrode 10 constituted an anode and the electrode 11 constituted a cathode, and limiting current characteristics were measured in the same way as in Example 1 to give limiting currents having a constant relationship with a hydrogen concentration in a gas measured. Table 6 shows the relationship between the hydrogen concentration and the limiting current value.

TABLE 6

| | Hydrogen concentration (ppm) | | | |
|---|---|---|---|---|
| | 100 | 500 | 1,000 | 3,000 |
| Limiting current (μA) | 1.7 | 10.5 | 22.0 | 77.6 |

It is further found that the above sensor had sensitivity not only to hydrogen but also to combustible gases such as carbon monoxide, ethanol, etc.

EXAMPLE 10

A fluorine gas sensor having a structure as shown in FIG. 6 was produced. Ion permeable layers 8 and 9 were formed by doping fluorine ion conducting $CaF_2$ with NaF, molding the doped material into disks having a diameter of 5 mm and thickness of 0.4 mm and sintering the disks. The ion permeable layer 8 was required to show a smaller ion permeation amount per unit time than the ion permeable layer 9. Therefore, the transport numbers thereof were changed by changing the NaF amount for the doping as follows. The ion permeable layer 8 had been formed by doping the ion conducting $CaF_2$ with 0.5% of NaF, and the ion permeable layer 9 had been formed by doping $CaF_2$ with 1% of NaF. Porous electrodes 10 and 11 and porous conductor layers 12 and 18 were formed by screen-printing platinum and baking the printed material at 800° C. A detection portion and an ion permeable layer were bonded with a glass 7, and the end portion thereof was sealed with a glass 14. These glass members were so densified by sintering them at 620° C. as to prevent gas permeation.

A direct current voltage 16 was applied to a heater 13 to heat the sensor element to 450° C. And in order to promote ionization on the conductor layer 12, 1 V of a direct voltage 22 was applied between the conductor layers 12 and 18 which were formed on surfaces of a gas G control screen.

Again in this sensor, a direct current voltage 5 was applied such that the electrode 10 constituted an anode and the electrode 11 constituted a cathode, and limiting current characteristics were measured in the same way as in Example 1 to give limiting current values having a constant relationship with a fluorine gas concentration in a gas measured. Table 7 shows the relationship between the fluorine gas concentration and the limiting current value.

TABLE 7

| | Fluorine concentration (ppm) | | | |
|---|---|---|---|---|
| | 500 | 1,000 | 5,000 | 8,000 |
| Limiting current ($\mu A$) | 4.2 | 7.5 | 43.2 | 70.5 |

As is clear from the above Examples, since the gas sensor of this invention electrochemically limits inflow of a gas with the ion permeable layer instead of using pores or a porous ceramic to limit gas diffusion, variability in characteristics depending upon production conditions is small, and no degradation in characteristics due to clogging of pores, etc., is observed. Thus, the gas sensor of this invention makes it possible to accurately measure a gas concentration in a wide range for a long period of time.

What is claimed is:

1. A solid electrolyte gas sensor for the measurement of a concentration of a gas to be detected in a gas mixture, which has:
   (A) a screen for controlling a permeation rate of the gas, which comprises;
      (a1) a first solid electrolytic membrane selectively permeable to ions derived from a specific gas to be detected, and
      (a2) a plurality of first porous conductors being present on both front and reverse surfaces of said first solid electrolytic membrane and electrically connected with each other so as to give a potential required for oxidation and reduction of said gas to be detected, said first porous conductor on the front surface and said first porous conductor on the reverse surface having an electrically different polarity from each other
   (B) a detection portion for detecting a permeation amount of ions derived from the gas to be detected, which comprises;
      (b1) a second solid electrolytic membrane selectively permeable to ions derived from a specific gas to be detected,
      (b2) a plurality of second porous conductors being present on both front and reverse surfaces of said second solid electrolytic membrane and electrically connected with each other so as to give a potential required for oxidation and reduction of said gas to be detected, said second porous conductor on the front surface and said second porous conductor on the reverse surface having an electrically different polarity from each other
      (b3) means of electrically measuring an amount of ions derived from the gas which permeates the second solid electrolytic membrane, and
   (C) a gas-tight space being adjacent to both said screen (A) and said detection portion (B); wherein
   (D) an amount of ions which permeate the first solid electrolytic membrane of the above screen (A) per unit time is smaller than an amount of ions which permeate the second solid electrolytic membrane of the above detection portion (B) per unit time under conditions that the sensor is in operation; and
   (E) all of ions which permeate the second solid electrolytic membrane of the above detection portion (B) are those which have permeated the first solid electrolytic membrane of the above screen (A).

2. A sensor according to claim 1, which is further provided with a space between the screen (A) and the front porous conductor of the detection portion (B) which faces the screen (A), the space being gastightly sealed.

3. A sensor according to claim 2, which is further provided with a porous insulating substance within the space.

4. A solid electrolyte gas sensor for the measurement of a concentration of a gas to be detected in a gas mixture, which has:
   (A) a screen for controlling a permeation rate of the gas, which comprises;
      (a1) a first solid electrolytic membrane selectively permeable to ions derived from a specific gas to be detected, and
      (a2) a plurality of first porous conductors being present on both front and reverse surfaces of said first solid electrolytic membrane and electrically connected with each other so as to give a potential required for oxidation and reduction of said gas to be detected, and
   (B) a detection portion for detecting a permeation amount of ions derived from the gas to be detected, which comprises;
      (b1) a second solid electrolytic membrane selectively permeable to ions derived from a specific gas to be detected,
      (b2) a plurality of second porous conductors being present on both front and reverse surfaces of said second solid electrolytic membrane and electrically connected with each other so as to give a potential required for oxidation and reduction of said gas to be detected, and
      (b3) means of electrically measuring an amount of ions derived from the gas which permeates the second solid electrolytic membrane; wherein:
   (C) an amount of ions which permeate the first solid electrolytic membrane of the above screen (A) per unit time is smaller than an amount of ions which permeate the second solid electrolytic membrane of the above detection portion (B) per unit time under conditions that the sensor is in operation; and
   (D) all of ions which permeate the second solid electrolytic membrane of the above detection portion (B) are those which have permeated the first solid electrolytic membrane of the above screen (A), wherein one of the first porous conductors of the screen (A) and one of the second porous conductors of the detection portion (B) are formed integrally as a unitary structure.

5. A sensor according to claim 1, wherein the first solid electrolytic membrane of the screen (A) and the second solid electrolytic membrane of the detection portion (B) are formed integrally as a unitary structure.

6. A solid electrolyte gas sensor for the measurement of a concentration of a gas to be detected in a gas mixture, which has:

(A) a screen for controlling a permeation rate of the gas, which comprises:
- (a1) a first solid electrolytic membrane selectively permeable to ions derived from a specific gas to be detected, and
- (a2) a plurality of first porous conductors being present on both front and reverse surfaces of said first solid electrolytic membrane and electrically connected with each other so as to give a potential required for oxidation and reduction of said gas to be detected, and (B) a detection portion for detecting a permeation amount of ions derived from the gas to be detected, which comprises:
- (b1) a second solid electrolytic membrane selectively permeable to ions derived from a specific gas to be detected,
- (b2) a plurality of second porous conductors being present on both front and reverse surfaces of said second solid electrolytic membrane and electrically connected with each other so as to give a potential required for oxidation and reduction of said gas to be detected, and
- (b3) means of electrically measuring an amount of ions derived from the gas which permeates the second solid electrolytic membrane; wherein:

(C) an amount of ions which permeate the first solid electrolytic membrane of the above screen (A) per unit time is smaller than an amount of ions which permeate the second solid electrolytic membrane of the above detection portion (B) per unit time under conditions that the sensor is in operation: and (D) all of ions which permeate the second solid electrolytic membrane of the above detection portion (B) are those which have permeated the first solid electrolytic membrane of the above screen (A), wherein a plurality of the first porous conductors of the screen (A) are connected to each other with a conductor and the screen (A) forms a concentration cell using, as a medium, ions derived from a gas to be detected.

7. A sensor according to claim 1, which is further provided with a mechanism in which a voltage required for electrolysis of a gas to be detected is applied between a plurality of the first porous conductors electrically connected to each other in the screen (A).

8. A sensor according to claim 1, which is further provided with an externally heating mechanism.

9. A sensor according to claim 1, wherein the means (b3) of the detection portion (B) is a current measuring means.

10. A sensor according to claim 1, wherein the gas to be detected is oxygen.

11. A method of measuring a concentration of a gas to be detected in a gas mixture, which comprises:
(1) feeding a gas mixture containing a gas to be detected onto one of a plurality of first porous conductors of a screen for control of a permeation rate of the gas, thereby to allow the gas to pass through the screen, said screen comprising:
- (a1) a first solid electrolytic membrane, which is selectively permeable to ions derived from a specific gas to be detected, and
- (a2) a plurality of the first porous conductors, which are present on both front and reverse surfaces of said first solid electrolytic membrane and electrically connected with each other so as to give a potential required for oxidation and reduction of said gas to be detected, (2) feeding said gas, which has passed the screen, onto one of a plurality of second porous conductors of a detection portion for detecting a permeation amount of ions derived from the gas to be detected thereby to allow the gas to pass through a second solid electrolytic membrane and a plurality of the second porous conductors at a higher rate than the gas is fed: the detection portion comprising,
- (b1) the second solid electrolytic membrane, which is selectively permeable to ions derived from a specific gas to be detected,
- (b2) a plurality of the second porous conductors, which are present on both front and reverse surfaces of said second solid electrolytic membrane and electrically connected with each other so as to give a potential required for oxidation and reduction of said gas to be detected, and
- (b3) means of electrically measuring an amount of ions derived from the gas which permeates the second solid electrolytic membrane; and (3) detecting an amount of the gas which has passed at the above step (2) with the above means (b3).

* * * * *